(12) United States Patent
Miyakawa et al.

(10) Patent No.: US 12,138,325 B2
(45) Date of Patent: Nov. 12, 2024

(54) DENTAL COMPOSITION

(71) Applicant: KURARAY NORITAKE DENTAL INC., Kurashiki (JP)

(72) Inventors: Hayato Miyakawa, Niigata (JP); Hirotaka Horiguchi, Niigata (JP); Tatsuya Kajikawa, Niigata (JP)

(73) Assignee: KURARAY NORITAKE DENTAL INC., Kurashiki (JP)

(*) Notice: Subject to any disclaimer, the term of this patent is extended or adjusted under 35 U.S.C. 154(b) by 687 days.

(21) Appl. No.: 17/296,007

(22) PCT Filed: Nov. 26, 2019

(86) PCT No.: PCT/JP2019/046246
§ 371 (c)(1),
(2) Date: May 21, 2021

(87) PCT Pub. No.: WO2020/111079
PCT Pub. Date: Jun. 4, 2020

(65) Prior Publication Data
US 2022/0008297 A1    Jan. 13, 2022

(30) Foreign Application Priority Data
Nov. 27, 2018 (JP) .................................. 2018-221371

(51) Int. Cl.
*A61K 6/887* (2020.01)
(52) U.S. Cl.
CPC .................................. *A61K 6/887* (2020.01)
(58) Field of Classification Search
CPC .................................................... A61K 6/887
See application file for complete search history.

(56) References Cited

U.S. PATENT DOCUMENTS

| | | |
|---|---|---|
| 2013/0172441 A1 | 7/2013 | Takahata et al. |
| 2017/0135909 A1 | 5/2017 | Takei et al. |
| 2017/0224591 A1 | 8/2017 | Vogel et al. |
| 2018/0110683 A1 | 4/2018 | Yoshinaga et al. |
| 2018/0228580 A1 | 8/2018 | Oldenburger et al. |
| 2018/0271629 A1 | 9/2018 | Maletz et al. |
| 2020/0253835 A1 | 8/2020 | Yamagawa et al. |

FOREIGN PATENT DOCUMENTS

| | | |
|---|---|---|
| DE | 20 2008 018 436 U1 | 1/2014 |
| JP | 2002-518419 A | 6/2002 |
| JP | 2006-83101 A | 3/2006 |
| JP | 2007-126417 A | 5/2007 |
| JP | 2018-153635 A | 10/2018 |
| JP | WO 2019/054507 A1 | 3/2019 |
| JP | 2019-112322 A | 7/2019 |
| JP | 2019-178105 A | 10/2019 |
| WO | WO 99/66880 A1 | 12/1999 |
| WO | WO 2012/042911 A1 | 4/2012 |
| WO | WO 2015/190100 A1 | 12/2015 |
| WO | WO 2017/136374 A1 | 8/2017 |

OTHER PUBLICATIONS

Extended European Search Report issued Jul. 15, 2022 in European Patent Application No. 19891442.6, 8 pages.
Presentation of publications issued Jul. 19, 2022 in Japanese Patent Application No. 2020-557747 (with English translation), 77 pages.
International Search Report issued Feb. 25, 2020 in PCT/JP2019/046246 filed Nov. 26, 2019.
Hirabayashi, S., et al., "Synthesis of Monomers for Dental Light-cured Composite Resins and Physical Properties of These Bulk Polymers", The Japanese Society for Dental Materials and Devices, vol. 7, No. 2, 1988, pp. 197-204.

*Primary Examiner* — Patrick D Niland
(74) *Attorney, Agent, or Firm* — Oblon, McClelland, Maier & Neustadt, L.L.P.

(57) ABSTRACT

A dental composition may have good handling properties and low polymerization shrinkage stress, and be capable of producing a cured product having desirable mechanical strength and excellent transparency. A dental composition may include a polymerizable monomer (A), a filler (B), and a polymerization initiator (C), wherein the polymerizable monomer (A) includes a polyfunctional (meth)acrylic monomer (a-1) having an aromatic ring but no hydroxyl group, and a polyfunctional (meth)acrylic monomer (a-2) having an alicyclic skeleton, and the polyfunctional (meth)acrylic monomer (a-1) and the polyfunctional (meth)acrylic monomer (a-2) have a mass ratio (a-1)/(a-2) of 30/70 to 95/5.

20 Claims, No Drawings

DENTAL COMPOSITION

CROSS-REFERENCE TO RELATED APPLICATIONS

The present application is the national stage of international application PCT/JP2019/046246, filed on Nov. 26, 2019, and claims the benefit of the filing date of Japanese Appl. No. 2018-221371, filed on Nov. 27, 2018.

TECHNICAL FIELD

The present invention relates to dental compositions.

BACKGROUND ART

In a cured form, dental compositions such as composite resins require high mechanical strength that can withstand the high occlusal pressure exerted by masticatory movements such as chewing. Dental compositions also have other requirements, including a certain degree of transparency needed to impart shades similar to the shades of natural teeth, and opacity to X rays (radiopacity) needed for recognition of restored sites.

A dental composition typically contains a filler, and a dental composition with a higher proportion of filler usually provides a higher mechanical strength in the cured product. An inorganic filler containing a heavy metal element such as barium glass is also commonly blended to develop opacity to X rays. Inorganic fillers used for this purpose usually have a refractive index of 1.50 to 1.58.

Because a dental composition requires transparency to provide shades similar to the shades of natural teeth, the filler and the matrix must have about the same refractive index. That is, when the inorganic filler used for a dental composition has a refractive index of 1.50 to 1.58, the matrix must have a refractive index of about 1.50 to 1.58 upon cure. Methods are known that use specific aromatic di(meth) acrylates to provide a dental composition having a matrix with a refractive index confined in such a range (see, for example, Patent Literatures 1 and 2).

CITATION LIST

Patent Literature

Patent Literature 1: JP 2007-126417 A
Patent Literature 2: JP 2002-518419 T

SUMMARY OF INVENTION

Technical Problem

In shaping a dental composition into a reproduced tooth form, good handling properties are often required for the dental composition (paste) so that the dental composition does not easily stick to a dental instrument such as a filling instrument. It is also desirable to reduce the polymerization shrinkage stress as much as possible. This is because a dental composition with a high polymerization shrinkage stress creates a gap at its interface with a cavity surface upon being cured after filling the cavity. This increases the risk of detachment of the cured product or the risk of secondary caries. However, by simply using the aromatic di(meth) acrylates described in Patent Literatures 1 and 2, it is difficult to obtain a dental composition having good handling properties and low polymerization shrinkage stress.

It is accordingly an object of the present invention to provide a dental composition having good handling properties and low polymerization shrinkage stress, and that is capable of producing a cured product having desirable mechanical strength and excellent transparency.

Solution to Problem

The present inventors conducted intensive studies to achieve the foregoing object, and found that a dental composition having good handling properties and low polymerization shrinkage stress, and that is capable of producing a cured product having desirable mechanical strength and excellent transparency can be obtained when a polyfunctional (meth)acrylic monomer having an aromatic ring but no hydroxyl group, and a polyfunctional (meth)acrylic monomer having an alicyclic skeleton are used as polymerizable monomers, and when the proportions of these monomers are confined within specific ranges. The present invention was completed after further studies based on this finding.

Specifically, the present invention relates to the following.

[1] A dental composition comprising a polymerizable monomer (A), a filler (B), and a polymerization initiator (C), wherein the polymerizable monomer (A) comprises a polyfunctional (meth)acrylic monomer (a-1) having an aromatic ring but no hydroxyl group, and a polyfunctional (meth)acrylic monomer (a-2) having an alicyclic skeleton, and the polyfunctional (meth)acrylic monomer (a-1) and the polyfunctional (meth)acrylic monomer (a-2) have a mass ratio (a-1)/(a-2) of 30/70 to 95/5.

[2] The dental composition according to [1], wherein the polyfunctional (meth)acrylic monomer (a-1) is an aromatic di(meth)acrylic acid ester represented by the following general formula (1),

[Chem. 1]

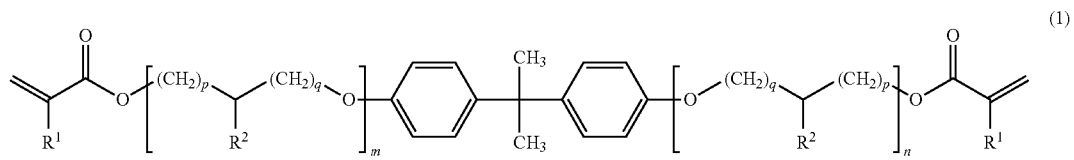

(1)

In general formula (1), $R^1$ represents a hydrogen atom or a methyl group, $R^2$ represents a hydrogen atom or an alkyl group having 1 to 3 carbon atoms, p and q each independently represent an integer of 0 to 6, m and n each independently represent an integer of 0 or more, wherein a plurality of $R^1$, $R^2$, p, and q each may be the same or different, and the average addition number of alkyleneoxy groups as represented by an average of the sum of m and n per molecule is 2 to 30.

[3] The dental composition according to [1], wherein the polyfunctional (meth)acrylic monomer (a-1) is 2,2-bis(4-methacryloyloxy(poly)ethoxyphenyl)propane (the average addition number of ethyleneoxy groups is 2 to 30).

[4] The dental composition according to any one of [1] to [3], wherein the total number of carbon atoms constituting the alicyclic skeleton of the polyfunctional (meth)acrylic monomer (a-2) is 5 to 20.

[5] The dental composition according to any one of [1] to [4], wherein the polyfunctional (meth)acrylic monomer (a-2) is at least one selected from the group consisting of tricyclo[5.2.1.0$^{2,6}$]decanedimethanol di(meth)acrylate and ethylene oxide-modified hydrogenated bisphenol A di(meth)acrylate.

[6] The dental composition according to any one of [1] to [5], wherein the dental composition has an adhesion of 4.0 N or less for a stainless steel plate at 25° C.

[7] The dental composition according to any one of [1] to [6], wherein the dental composition has a polymerization shrinkage stress of 12.0 MPa or less.

Advantageous Effects of Invention

The present invention can provide a dental composition having good handling properties and low polymerization shrinkage stress, and that is capable of producing a cured product having desirable mechanical strength and excellent transparency.

DESCRIPTION OF EMBODIMENTS

Dental Composition

A dental composition of the present invention comprises a polymerizable monomer (A), a filler (B), and a polymerization initiator (C), wherein the polymerizable monomer (A) comprises a polyfunctional (meth)acrylic monomer (a-1) having an aromatic ring but no hydroxyl group, and a polyfunctional (meth)acrylic monomer (a-2) having an alicyclic skeleton, and the polyfunctional (meth)acrylic monomer (a-1) and the polyfunctional (meth)acrylic monomer (a-2) have a mass ratio (a-1)/(a-2) of 30/70 to 95/5.

Polymerizable Monomer (A)

The polymerizable monomer (A) comprises a polyfunctional (meth)acrylic monomer (a-1) having an aromatic ring but no hydroxyl group, and a polyfunctional (meth)acrylic monomer (a-2) having an alicyclic skeleton.

Polyfunctional (meth)Acrylic Monomer (a-1)

The polyfunctional (meth)acrylic monomer (a-1) is not particularly limited, as long as it is a polyfunctional (meth)acrylic monomer having an aromatic ring but no hydroxyl group. Preferred for use are (meth)acrylic acid esters, (meth)acrylamides, and other such polymerizable monomers satisfying this requirement. In view of considerations such as past performance and safety as dental material, the polyfunctional (meth)acrylic monomer (a-1) is preferably a (meth)acrylic acid ester, more preferably a methacrylic acid ester.

The number of functional groups in the polyfunctional (meth)acrylic monomer (a-1) is not particularly limited, as long as the monomer is polyfunctional. However, in view of considerations such as the mechanical strength of the cured product obtained, the polyfunctional (meth)acrylic monomer (a-1) contains preferably 2 to 10, more preferably 2 to 6, even more preferably 2 to 4, particularly preferably 2 or 3, most preferably 2 (meth)acryloyl groups per molecule.

The type of the aromatic ring in the polyfunctional (meth)acrylic monomer (a-1) is not particularly limited, and may be, for example, a benzene ring, a naphthalene ring, an anthracene ring, a furan ring, a thiophene ring, a pyrrole ring, an imidazole ring, a pyridine ring, or a pyrimidine ring. The polyfunctional (meth)acrylic monomer (a-1) may have one of these aromatic rings, or two or more of these aromatic rings. Preferably, the aromatic ring is one consisting of carbon atoms and hydrogen atoms, more preferably a benzene ring.

The number of aromatic rings in the polyfunctional (meth)acrylic monomer (a-1) is not particularly limited, and the polyfunctional (meth)acrylic monomer (a-1) may have only one aromatic ring, or two or more aromatic rings. For advantages such as enhancement of the effectiveness of the present invention, the total number of carbon atoms constituting the aromatic ring in the polyfunctional (meth)acrylic monomer (a-1) is preferably 6 to 18, more preferably 6 to 12, even more preferably 12 carbon atoms.

For advantages such as enhancement of the effectiveness of the present invention, the polyfunctional (meth)acrylic monomer (a-1) is preferably an aromatic di(meth)acrylic acid ester represented by the following general formula (1).

[Chem. 2]

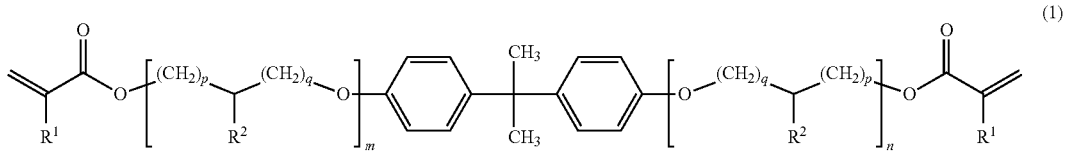

(1)

In the general formula (1), $R^1$ represents a hydrogen atom or a methyl group, $R^2$ represents a hydrogen atom or an alkyl group having 1 to 3 carbon atoms, p and q each independently represent an integer of 0 to 6, and m and n each independently represent an integer of 0 or more. A plurality of $R^1$, $R^2$, p, and q each may be the same or different. Taking $R^2$ as an example, a plurality of $R^2$ may be the same, or may be different either partly or completely. The same is the case for $R^1$, p, and q. The average addition number of alkyleneoxy groups as represented by an average of the sum of m and n per molecule is 2 to 30.

In the general formula (1), $R^1$ represents a hydrogen atom or a methyl group. In view of considerations such as past performance and safety as dental material, it is preferable that at least one of $R^1$ be a methyl group. More preferably, all of $R^1$ are methyl groups.

In the general formula (1), $R^2$ represents a hydrogen atom or an alkyl group having 1 to 3 carbon atoms. Examples of the alkyl group having 1 to 3 carbon atoms include a methyl group, an ethyl group, and an isopropyl group. For advantages such as enhancement of the effectiveness of the present invention, $R^2$ is preferably a hydrogen atom or a methyl group, more preferably a hydrogen atom.

In the general formula (1), p and q each independently represent an integer of 0 to 6. For advantages such as enhancement of the effectiveness of the present invention, the total of p and q in each unit represented by $[-(CH_2)_p-CHR^2-(CH_2)_q-O-]$ in general formula (1) is preferably 0 to 10, more preferably 1 to 7, even more preferably 1 to 3, particularly preferably 1 or 2, most preferably 1.

In the general formula (1), m and n each independently represent an integer of 0 or more. Preferably, m and n are each 0 to 30, more preferably 0 to 20, even more preferably 0 to 10.

In view of considerations such as the handling properties and polymerization shrinkage stress of the dental composition obtained, the average addition number of alkyleneoxy groups (for example, the average addition number of ethyleneoxy groups; described later) as represented by an average of the sum of m and n per molecule of an aromatic di(meth)acrylic acid ester represented by the general formula (1) is 2 to 30, preferably 2 to 20, more preferably 2 to 12, even more preferably 2 to 7, particularly preferably 2 to 3, most preferably 2.1 to 2.9.

Specific examples of aromatic di(meth)acrylic acid esters represented by the general formula (1) include 2,2-bis(4-(meth)acryloyloxy(poly)ethoxyphenyl)propane (the average addition number of ethyleneoxy groups is 2 to 30). In view of considerations such as past performance and safety as dental material, 2,2-bis(4-methacryloyloxy(poly)ethoxyphenyl)propane (the average addition number of ethyleneoxy groups is 2 to 30) is preferred. The 4-(meth)acryloyloxy(poly)ethoxyphenyl groups in 2,2-bis(4-(meth)acryloyloxy(poly)ethoxyphenyl)propane may be 4-(meth)acryloyloxyethoxyphenyl groups or 4-(meth)acryloyloxypolyethoxyphenyl groups. One of the two 4-(meth)acryloyloxy(poly)ethoxyphenyl groups in 2,2-bis(4-methacryloyloxy(poly)ethoxyphenyl)propane may be a 4-(meth)acryloyloxyethoxyphenyl group, and the other may be a 4-(meth)acryloyloxypolyethoxyphenyl group. In view of the paste properties of the dental composition and the mechanical strength of the cured product obtained, it is particularly preferable that the 2,2-bis(4-(meth)acryloyloxy(poly)ethoxyphenyl)propane comprise at least one selected from the group consisting of 2,2-bis(4-(meth)acryloyloxyethoxyphenyl)propane, 2-(4-(meth)acryloyloxydiethoxyphenyl)-2-(4-(meth)acryloyloxyethoxyphenyl)propane, and 2,2-bis(4-(meth)acryloyloxydiethoxyphenyl)propane.

Polyfunctional (meth)Acrylic Monomer (a-2)

The polyfunctional (meth)acrylic monomer (a-2) may be a polyfunctional (meth)acrylic monomer having at least one alicyclic skeleton, and that does not classify as the polyfunctional (meth)acrylic monomer (a-1). Preferred for use are, for example, (meth)acrylic acid esters, (meth)acrylamides, and other such polymerizable monomers satisfying this requirement. In view of considerations such as past performance and safety as dental material, the polyfunctional (meth)acrylic monomer (a-2) is preferably a (meth)acrylic acid ester, more preferably a methacrylic acid ester.

The number of functional groups in the polyfunctional (meth)acrylic monomer (a-2) is not particularly limited, as long as the monomer is polyfunctional. However, in view of considerations such as the mechanical strength of the cured product obtained, the polyfunctional (meth)acrylic monomer (a-2) contains preferably 2 to 10, more preferably 2 to 6, even more preferably 2 to 4, particularly preferably 2 or 3, most preferably 2 (meth)acryloyl groups per molecule.

The alicyclic skeleton of the polyfunctional (meth)acrylic monomer (a-2) is not particularly limited, and may be any of a variety of alicyclic skeletons that do not belong to aromatic rings. Preferably, the alicyclic skeleton consists of carbon atoms and hydrogen atoms. However, the alicyclic skeleton may be a heterocyclic skeleton in which some of the carbon atoms of the alicyclic skeleton are substituted with heteroatoms such as nitrogen, oxygen, and sulfur atoms. Preferably, the alicyclic skeleton is a saturated group with no unsaturated bond. However, the alicyclic skeleton may be an unsaturated group having an unsaturated bond.

Specific examples of the alicyclic skeleton consisting of carbon atoms and hydrogen atoms include monocyclic hydrocarbon rings and polycyclic hydrocarbon rings. Examples of the monocyclic hydrocarbon rings include cycloalkane rings such as a cyclopentane ring, a cyclohexane ring, and a cyclooctane ring; and cycloalkene rings such as a cyclopentene ring, a cyclohexene ring, and a cyclooctadiene ring. Examples of the polycyclic hydrocarbon rings include polycyclic cycloalkane rings having no spiro structure, for example, such as a tricyclodecane ring (e.g., a tricyclo[5.2.1.0$^{2,6}$]decane ring), a norbornane ring, an adamantane ring, and a decahydronaphthalene ring; and spiro rings such as a spiro[3.4]octane ring, a spiro[4.4]nonane ring, and a spiro[4.5]decane ring. In view of considerations such as the polymerization shrinkage stress of the dental composition obtained, the alicyclic skeleton consisting of carbon atoms and hydrogen atoms is preferably a polycyclic hydrocarbon ring, more preferably a polycyclic cycloalkane ring having no Spiro structure. The polycyclic hydrocarbon ring has preferably 2 to 4 rings, more preferably 2 or 3 rings, even more preferably 3 rings. Specific examples of the heterocyclic skeleton include a tetrahydrofuran ring, a tetrahydropyran ring, an imidazolidine ring, a piperidine ring, and a morpholine ring.

In the polyfunctional (meth)acrylic monomer (a-2), the alicyclic skeleton may exist as a monovalent group, a divalent group, or a group with higher valency. Preferably, the alicyclic skeleton exists as a divalent group. When the alicyclic skeleton exists as a divalent group or a group with higher valency, some of the binding sites may be binding to a substituent such as an alkyl group, for example, such as in an isobornane ring.

The number of alicyclic skeletons in the polyfunctional (meth)acrylic monomer (a-2) is not particularly limited, and the polyfunctional (meth)acrylic monomer (a-2) may have only one alicyclic skeleton, or may have two or more alicyclic skeletons. For advantages such as enhancement of the effectiveness of the present invention, the total number of carbon atoms constituting the alicyclic skeleton of the polyfunctional (meth)acrylic monomer (a-2) is preferably 5 to 20, more preferably 6 to 18, even more preferably 8 to 12, particularly preferably 9 to 11 carbon atoms.

In view of considerations such as the mechanical strength of the cured product obtained, the polyfunctional (meth)acrylic monomer (a-2) is preferably at least one selected from the group consisting of tricyclo[5.2.1.0$^{2,6}$]decanedimethanol di(meth)acrylate and ethylene oxide-modified hydrogenated bisphenol A di(meth)acrylate. More preferably, the polyfunctional (meth)acrylic monomer (a-2) is tricyclo [5.2.1.0$^{2,6}$]decanedimethanol di(meth)acrylate.

In the polymerizable monomer (A), the polyfunctional (meth)acrylic monomer (a-1) and the polyfunctional (meth)acrylic monomer (a-2) must have a mass ratio (a-1)/(a-2) of 30/70 to 95/5. In this way, the cured product obtained can have desirable mechanical strength and excellent transparency, and the dental composition produced can have good handling properties and low polymerization shrinkage stress. In view of these considerations, the mass ratio (a-1)/(a-2) is preferably at least 40/60, more preferably at least 45/55, even more preferably at least 50/50, and is preferably at most 90/10, more preferably at most 85/15, even more preferably at most 70/30.

The polymerizable monomer (A) may consist of the polyfunctional (meth)acrylic monomer (a-1) and the polyfunctional (meth)acrylic monomer (a-2). However, the polymerizable monomer (A) may comprise other polymerizable monomers, in addition to the polyfunctional (meth)acrylic monomer (a-1) and the polyfunctional (meth)acrylic monomer (a-2). In view of considerations such as the polymerization shrinkage stress of the dental composition obtained, the total content of polyfunctional (meth)acrylic monomer (a-1) and polyfunctional (meth)acrylic monomer (a-2) in the polymerizable monomer (A) is preferably 70 mass % or more, more preferably 80 mass % or more, even more preferably 90 mass % or more, particularly preferably 100 mass %.

The additional polymerizable monomers may be known polymerizable monomers used for dental materials. Examples of such polymerizable monomers include esters of carboxylic acids such as α-cyanoacrylic acid, (meth)acrylic acid, α-halogenated acrylic acid, crotonic acid, cinnamic acid, sorbic acid, maleic acid, and itaconic acid; (meth)acrylamides; derivatives of (meth)acrylamides; vinyl esters; vinyl ethers; mono-N-vinyl derivatives; and derivatives of styrene. The additional polymerizable monomers may be used alone, or two or more thereof may be used in combination. The additional polymerizable monomers are preferably esters of carboxylic acids or derivatives of (meth)acrylamides, more preferably (meth)acrylic acid esters or derivatives of (meth)acrylamides, even more preferably (meth)acrylic acid esters. A dental composition of the present invention may comprise a polyfunctional (meth)acrylic monomer having an aromatic ring and a hydroxyl group, provided that the configurations of the present invention are satisfied. However, in view of considerations such as the handling properties of the dental composition obtained, it is preferable not to contain such a polyfunctional (meth)acrylic monomer in overly large amounts, and, more preferably, the dental composition is essentially free of a polyfunctional (meth)acrylic monomer having an aromatic ring and a hydroxyl group. In the polymerizable monomer (A), the content of a polyfunctional (meth)acrylic monomer having an aromatic ring and a hydroxyl group is preferably 10 mass % or less, more preferably 5 mass % or less, even more preferably 2 mass % or less, particularly preferably 0 mass %.

Examples of the (meth)acrylic acid esters as additional polymerizable monomers are as follows.

(i) Monofunctional (meth)acrylic Acid Esters

Alkyl(meth)acrylates, for example, such as methyl(meth)acrylate, ethyl(meth)acrylate, n-butyl(meth)acrylate, isobutyl(meth)acrylate, sec-butyl(meth)acrylate, t-butyg-meth)acrylate, pentyl(meth)acrylate, neopentyl(meth)acrylate, isoamyl(meth)acrylate, hexyl(meth)acrylate, heptyl (meth)acrylate, octyl(meth)acrylate, 2-ethylhexyl(meth)acrylate, n-octyl(meth)acrylate, isooctyl(meth)acrylate, nonyl(meth)acrylate, isononyl(meth)acrylate, decyl(meth)acrylate, isodecyl(meth)acrylate, undecyl(meth)acrylate, dodecyl(meth)acrylate, tridecyl(meth)acrylate, tetradecyl (meth)acrylate, pentadecyl(meth)acrylate, isomyristyl (meth)acrylate, hexadecyl(meth)acrylate, heptadecyl(meth)acrylate, octadecyl(meth)acrylate, nonadecyl(meth)acrylate, eicodecyl(meth)acrylate, 2-hydroxyethyl(meth)acrylate, 2-hydroxypropyl(meth)acrylate, 2-hydroxybutygmeth)acrylate, 2-hydroxy-3-phenyloxypropyl(meth)acrylate, 4-hydroxybutyl(meth)acrylate, 1,6-hexanediol mono(meth)acrylate, and neopentyl glycol mono(meth)acrylate Alicyclic (meth)acrylates, for example, such as (meth)acryloylmorpholine, cyclohexyl(meth)acrylate, dicyclopentenyl(meth)acrylate, dicyclopentenyloxyethyl(meth)acrylate, dicyclopentanyl(meth)acrylate, isobornyl(meth) acrylate, and 4-hydroxycyclohexyl(meth)acrylate Aromatic (meth)acrylates, for example, such as phenyl (meth)acrylate and benzyl(meth)acrylate (ii) Bifunctional (meth)acrylic Acid Esters Ethylene glycol di(meth)acrylate, triethylene glycol diacrylate, triethylene glycol dimethacrylate (commonly known as TEGDMA), propylene glycol di(meth)acrylate, neopentyl glycol di(meth)acrylate, 1,6-hexanediol di(meth)acrylate, 1,10-decanediol di(meth)acrylate, 2,2-bis[4-(3-acryloyloxy-2-hydroxypropoxy)phenyl]propane, 2,2-bis[4-(3-methacryloyloxy-2-hydroxypropoxy)phenyl]propane (commonly known as Bis-GMA), 1,2-bis[3-(meth)acryloyloxy-2-hydroxypropoxy]ethane, pentaerythritol di(meth)acrylate, [2,2,4-trimethylhexamethylenebis(2-carbamoyloxyethyl)]dimethacrylate (commonly known as UDMA), and 2,2,3,3,4,4-hexafluoro-1,5-pentyl di(meth)acrylate (iii) Tri- and Higher-Functional (meth)acrylic Acid Esters Trimethylolpropane tri(meth)acrylate, trimethylolethane tri(meth)acrylate, tetramethylolmethane tri(meth)acrylate, pentaerythritol tetra(meth)acrylate, dipentaerythritol hexa (meth)acrylate, N,N'-(2,2,4-trimethylhexamethylene)bis[2-(aminocarboxy)propane-1,3-diol]tetra(meth)acrylate, and 1,7-di(meth)acryloyloxy-2,2,6,6-tetra(meth)acryloyloxymethyl-4-oxaheptane In view of providing a dental composition having desirable adhesive properties for tooth structure and prostheses, the additional polymerizable monomer may be a monomer having an acidic group. Examples of such a monomer having an acidic group include a polymerizable monomer having at least one acidic group such as a phosphoric acid group, a pyrophosphoric acid group, a thiophosphoric acid group, a phosphonic acid group, a sulfonic acid group, and a carboxylic acid group. Specific examples include (meth)acrylic acid esters having such acidic groups, and (meth)acrylamides having such acidic groups.

Examples of the polymerizable monomer having a phosphoric acid group include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, ammonium salts of these.

Examples of polymerizable monomers having acidic groups other than acidic groups such as the pyrophosphoric acid group, thiophosphoric acid group, phosphonic acid group, sulfonic acid group, and carboxylic acid group above include those mentioned in WO2012/042911.

In view of considerations such as the polymerization shrinkage stress of the dental composition obtained, the content of the additional polymerizable monomer in the polymerizable monomer (A) is preferably 30 mass % or less, more preferably 20 mass % or less, even more preferably 10 mass % or less, particularly preferably 0 mass %.

Filler (B)

A dental composition of the present invention comprises a filler (B). The filler (B) may be a known inorganic filler used as a filler for dental compositions. Examples of such inorganic fillers include various types of glasses (for example, glasses containing boron and/or aluminum and various heavy metals with the main component silicon dioxide (e.g., quartz, fused quartz, silica gel) or silicon), alumina, various types of ceramics, diatomaceous earth, kaolin, clay minerals (e.g., montmorillonite), activated earth, synthetic zeolite, mica, silica, calcium fluoride, ytterbium fluoride, calcium phosphate, barium sulfate, zirconium dioxide (zirconia), titanium dioxide (titania), and hydroxyapatite.

The shape of the inorganic filler is not particularly limited, and the inorganic filler may be a powder of irregularly shaped or spherical particles. An irregularly shaped inorganic filler improves the mechanical strength and wear resistance of the cured product obtained. A spherical inorganic filler improves the gloss polishability and gloss retention of the cured product obtained. The shape of inorganic filler may be appropriately selected according to the intended use of the dental composition obtained.

The inorganic filler has an average particle diameter of preferably 0.001 to 50 µm, more preferably 0.01 to 10 µm, even more preferably 0.1 to 5 µm, particularly preferably 0.15 to 3 µm. The average particle diameter of filler (B) such as an inorganic filler may be a median value of a volume particle size distribution obtained by dispersing the filler (B) in at least one dispersion medium selected from alcohol and water, and measuring the particles with a laser diffraction particle size distribution analyzer such as SALD-2300 manufactured by Shimadzu Corporation. For fillers (B) with a small average particle diameter below the lower limit of measurement (for example, 0.10 µm) by the laser diffraction particle size distribution analyzer, the average particle diameter may be a mean value of the particle diameters of randomly selected 20 particles in an electron micrograph taken with an electron microscope such as SU3500 or SU9000 manufactured by Hitachi, Ltd. For nonspherical particles, the particle diameter may be an arithmetic mean value of the maximum and minimum lengths of particles.

The inorganic filler may be an agglomerated particle formed by particle agglomeration. Commercially available inorganic fillers typically exist in the form of aggregates. The cohesion of commercially available inorganic fillers is so weak that these fillers break into particle sizes indicated by the manufacturer when 10 mg of its powder is added and ultrasonically dispersed at 40 W and 39 KHz for 30 minutes in 300 mL of water or in the same amount of a dispersion medium prepared by adding a surfactant (e.g., at most 5 mass % of sodium hexametaphosphate) to water. In contrast, the particles in the agglomerate mentioned above are strongly held together, and become hardly dispersed even under these conditions.

In a preferred method of preparing a strong agglomerate of particles from an aggregate of commercially available inorganic fillers, the inorganic filler is heated to a temperature range just below the temperature that melts the inorganic filler so that the adjoining inorganic filler particles under the applied heat lightly fuse together. Here, the inorganic filler may be heated after forming an aggregate, in order to control the shape of the agglomerated particle. An aggregate can be formed, for example, by applying pressure to the inorganic filler placed in a suitable container, or by dispersing the inorganic filler in a solvent, and removing the solvent using a method such as spray drying.

In another preferred method of preparing an agglomerated particle, a sol such as a silica sol, an alumina sol, a titania sol, or a zirconia sol prepared by using a wet method is dried using a method such as freeze drying or spray drying, and optionally subjected to a heat treatment. Specific examples of the sols include Seahostar manufactured by Nippon Shokubai Co., Ltd., OSCAL and QUEEN TITANIC manufactured by JGC C & C, and Snowtwx, Aluminasol, Celnax, and NanoUse manufactured by Nissan Chemical Industries, Ltd.

The filler (B) in a dental composition of the present invention may be an organic filler, or an organic-inorganic composite filler (a filler containing an inorganic filler and a polymer of polymerizable monomer) obtained by, for example, adding a polymerizable monomer to the inorganic filler, and pulverizing the composite filler after polymerization and curing.

Examples of materials of the organic filler include polymethylmethacrylate, polyethylmethacrylate, a methyl methacrylate-ethyl methacrylate copolymer, crosslinked polymethylmethacrylate, crosslinked polyethylmethacrylate, polyamides, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone, or two or more thereof may be used in combination. In view of considerations such as the handling properties of the dental composition and the mechanical strength of the cured product obtained, the average particle diameter of the organic filler is preferably 0.0005 to 50 µm, more preferably 0.001 to 10 µm.

The organic-inorganic composite filler is preferably one in which inorganic particles having an average particle diameter of 0.5 µm or less are dispersed in an organic matrix.

The method of fabrication is not particularly limited. For example, the organic-inorganic composite filler can be prepared by adding a known polymerizable monomer and a known polymerization initiator to the inorganic filler, polymerizing the filler mixture in paste form by a polymerization method such as solution polymerization, suspension polymerization, emulsion polymerization, or bulk polymerization, and pulverizing the resulting polymer.

The organic-inorganic composite filler has an average particle diameter of preferably 1 to 50 μm, more preferably 3 to 25 μm. By setting these lower limits for the average particle diameter of organic-inorganic composite filler, the dental composition obtained becomes less sticky, and handling properties improve. By setting the foregoing upper limits for the average particle diameter of organic-inorganic composite filler, the dental composition obtained can have reduced roughness and reduced dryness, and handling properties improve.

The filler (B) may be used alone, or two or more thereof may be used in combination. For advantages such as enhancement of the effectiveness of the present invention, the filler (B) is preferably an inorganic filler and/or an organic-inorganic composite filler, more preferably an inorganic filler, even more preferably glass. In order to develop X-ray opacity in the cured product, particularly preferred for use as filler (B) is an inorganic filler (or may be any of the glasses above) containing a heavy metal element such as zirconium, barium, titanium, lanthanum, or strontium.

Examples of inorganic fillers capable of imparting X-ray opacity include barium borosilicate glass (for example, E3000 manufactured by Esstech, and 8235, GM27884, and GM39923 manufactured by Schott), strontium boroaluminosilicate glass (for example, E4000 manufactured by Esstech, and G018-093 and GM32087 manufactured by Schott), lanthanum glass (for example, GM31684 manufactured by Schott), fluoroaluminosilicate glass (for example, G018-091 and G018-117 manufactured by Schott), zirconia-containing glass (for example, G018-310 and G018-159 manufactured by Schott), strontium-containing glass (for example, G018-163, G018-093, and GM32087 manufactured by Schott), zinc oxide-containing glass (for example, G018-161 manufactured by Schott), and calcium-containing glass (for example, G018-309 manufactured by Schott).

Preferably, the filler (B) is subjected to a surface treatment in advance with a surface treatment agent, in order to improve compatibility to the polymerizable monomer (A), or to improve the mechanical strength of the cured product by increasing the chemical binding properties for polymerizable monomer (A). The surface treatment agent may be a known surface treatment agent, for example, such as vinyltrimethoxysilane, vinyltriethoxysilane, vinyltrichlorosilane, vinyltri (β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, or γ-aminopropyltriethoxysilane. The concentration of surface treatment agent is typically 0.1 to 30 mass %, preferably 1 to 20 mass % relative to the filler (B). The surface treatment method is not limited to specific methods, and may be appropriately selected from known methods.

The content of filler (B) in a dental composition of the present invention is not particularly limited, and may be, for example, at least 10 parts by mass, at least 30 parts by mass, or at least 80 parts by mass relative to 100 parts by mass of polymerizable monomer (A). However, in view of considerations such as the mechanical strength of the cured product obtained, the content of filler (B) is preferably at least 150 parts by mass, more preferably at least 190 parts by mass, even more preferably at least 240 parts by mass, and is preferably at most 900 parts by mass, more preferably at most 700 parts by mass, even more preferably at most 570 parts by mass relative to 100 parts by mass of polymerizable monomer (A).

Polymerization Initiator (C)

A dental composition of the present invention comprises a polymerization initiator (C). The polymerization initiator (C) may be a common polymerization initiator, preferably a polymerization initiator used in dentistry. For example, the polymerization initiator (C) may be at least one selected from the group consisting of a photopolymerization initiator and a chemical polymerization initiator. The polymerization initiator (C) is preferably a photopolymerization initiator.

Examples of the photopolymerization initiator include (bis)acylphosphine oxides (including salts), thioxanthones (including salts such as quaternary ammonium salts), ketals, α-diketones, benzoin alkyl ethers, and α-aminoketones.

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2,6-dimethylphenyl)phosphonate, and salts thereof (for example, sodium salts, potassium salts, lithium salts, and ammonium salts; more specifically, sodium salts of 2,4,6-trimethylbenzoylphenylphosphine oxide, potassium salts of 2,4,6-trimethylbenzoyldiphenylphosphine oxide, and ammonium salts of 2,4,6-trimethylbenzoyldiphenylphosphine oxide).

Examples of bisacylphosphine oxides in the (bis)acylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphine oxide, and salts thereof (such as sodium salts, potassium salts, lithium salts, and ammonium salts).

Preferred among these (bis)acylphosphine oxides are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of the thioxanthones include thioxanthone, 2-chlorothioxanthen-9-one, 2-hydroxy-3-(9-oxo-9H-thioxanthen-4-yloxy)-N,N,N-trimethylpropaneaminium chloride, 2-hydroxy-3-(1-methyl-9-oxo-9H-thioxanthen-4-yloxy)-N,N,N-trimethyl-1-propaneaminium chloride, 2-hydroxy-3-(9-oxo-9H-thioxanthen-2-yloxy)-N,N,N-trimethyl-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Preferred among these thioxanthones are 2-chlorothioxanthen-9-one, and 2-hydroxy-3-(3,4-dimethyl-9H-thioxanthen-2-yloxy)-N,N,N-trimethyl-1-propaneaminium chloride.

Examples of the ketals include benzyl dimethyl ketal, and benzyl diethyl ketal.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Preferred is camphorquinone for its maximum absorption wavelength occurring in the visible light region.

Examples of the benzoinalkyl ethers include benzoin methyl ether, benzoin ethyl ether, benzoin isopropyl ether, and benzoin isobutyl ether.

Examples of the α-aminoketones include 2-methyl-1-[4-(methylthio)phenyl]-2-morpholinopropan-1-one.

Preferred among these photopolymerization initiators is at least one selected from the group consisting of a (bis)acylphosphine oxide and an α-diketone.

The chemical polymerization initiator may be a known chemical polymerization initiator, preferably, for example, an azo compound or an organic peroxide. Examples of the azo compound include azobisisobutyronitrile. Examples of the organic peroxide include ketone peroxides, hydroperoxides, diacyl peroxides, &alkyl peroxides, peroxy ketals, peroxyesters, and peroxydicarbonates.

Examples of the ketone peroxides include methyl ethyl ketone peroxide, methyl isobutyl ketone peroxide, methyl cyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxy ketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxyesters include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxyvalerate.

Examples of the peroxydicarbonates include di-3-methoxyperoxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

From an overall balance of safety, storage stability, and radical generating potential, preferred among these organic peroxides are diacyl peroxides, more preferably benzoyl peroxide.

The content of polymerization initiator (C) in a dental composition of the present invention is preferably at least 0.01 parts by mass, more preferably at least 0.1 parts by mass, even more preferably at least 0.15 parts by mass, particularly preferably at least 0.3 parts by mass, and is preferably at most 10 parts by mass, more preferably at most 7 parts by mass, even more preferably at most 6 parts by mass, particularly preferably at most 5 parts by mass relative to 100 parts by mass of polymerizable monomer (A).

Polymerization Accelerator

A dental composition of the present invention may further comprise a polymerization accelerator. The polymerization accelerator may be a known polymerization accelerator. Examples include amines, sulfinic acids (including salts), aldehydes, and thiol compounds. The polymerization accelerator may be used alone, or two or more thereof may be used in combination.

The amines can be divided into aliphatic amines and aromatic amines. Examples of the aliphatic amines include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. In view of curability and storage stability of the dental composition, preferred are tertiary aliphatic amines, more preferably 2-(dimethylamino)ethyl methacrylate, N-methyldiethanolamine, and triethanolamine.

Examples of the aromatic amines include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, n-butoxyethyl 4-(N,N-dimethylamino)benzoate, 2-(methacryloyloxy)ethyl 4-(N,N-dimethylamino)benzoate, 4-(N,N-dimethylamino)benzophenone, and butyl 4-(N,N-dimethylamino)benzoate. In view of curability and other properties of the dental composition, preferred is at least one selected from the group consisting of N,N-bis(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone. More preferred is ethyl 4-(N,N-dimethylamino)ethyl benzoate.

Examples of the sulfinic acids include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Preferred are sodium benzenesulfinate, sodium p-toluenesulfinate, and sodium 2,4,6-triisopropylbenzenesulfinate.

Examples of the aldehydes include terephthalaldehyde, and derivatives of benzaldehyde. Examples of the derivatives of benzaldehyde include dimethylaminobenzaldehyde, p-methyloxybenzaldehyde, p-ethyloxybenzaldehyde, and p-n-octyloxybenzaldehyde. In view of curability and other properties of the dental composition, preferred is p-n-octyloxybenzaldehyde.

Examples of the thiol compounds include 3-mercaptopropyltrimethoxysilane, 2-mercaptobenzooxazole, decanethiol, and thiobenzoic acid.

Preferred among these polymerization accelerators are amines, more preferably aromatic amines.

The content of the polymerization accelerator in a dental composition of the present invention is not particularly limited, and is preferably at least 0.01 parts by mass, more preferably at least 0.1 parts by mass, even more preferably at least 0.2 parts by mass, and is preferably at most 10 parts by mass, more preferably at most 7 parts by mass, even more preferably at most 5 parts by mass relative to 100 parts by mass of polymerizable monomer (A).

Polymerization Inhibitor

A dental composition of the present invention may further comprise a polymerization inhibitor. Examples of the polymerization inhibitor include 3,5-di-t-butyl-4-hydroxytoluene, hydroquinone, dibutylhydroquinone, dibutylhydroquinone monomethyl ether, hydroquinone monomethyl ether, and 2,6-di-t-butylphenol. The polymerization inhibitors may be used alone, or two or more thereof may be used in combination.

The content of the polymerization inhibitor in a dental composition of the present invention is not particularly limited, and is preferably at least 0.01 parts by mass, more preferably at least 0.05 parts by mass, even more preferably at least 0.075 parts by mass, particularly preferably at least 0.1 parts by mass, and is preferably at most 10 parts by mass, more preferably at most 7 parts by mass, even more preferably at most 5 parts by mass, particularly preferably at most 3 parts by mass relative to 100 parts by mass of polymerizable monomer (A).

Other Components

Aside from the foregoing components, a dental composition of the present invention may additionally comprise other components such as pH adjusters, ultraviolet absorbers, antioxidants, antimicrobial agents, fluorescent agents, surface active agents, and dispersants, according to intended use, provided that such additional components do not interfere with the effects of the invention.

For advantages such as enhancement of the effectiveness of the present invention, the total content of the polymerizable monomer (A), the filler (B), and the polymerization initiator (C) as essential components of a dental composition of the present invention, and the polymerization accelerator and polymerization inhibitor contained as optional components is preferably 50 mass % or more, more preferably 80 mass % or more, even more preferably 95 mass % or more, particularly preferably 98 mass % or more. The total content of these essential and optional components may be 100 mass %.

Method of Production of Dental Composition

A method of preparation of a dental composition of the present invention is not particularly limited, and a dental composition of the present invention can be obtained by combining the components in predetermined amounts. The components may be combined in any order, at once or in two or more separate portions. Optionally, the components may be mixed or kneaded, or may be subjected to degassing, for example, vacuum degassing. The resultant dental composition may be charged into a single container (e.g., a syringe) to prepare a one-pack type dental composition.

Uses

A dental composition of the present invention can be used as a dental material, for example, such as a dental adhesive, a dental cement, a dental coating material, a dental composite resin, or a dental pretreatment agent for metals and ceramics. A dental composition of the present invention is suited as a dental material for replacing a natural tooth, in part or in whole. A dental composition of the present invention is particularly suited as a dental composite resin.

EXAMPLES

The following describes the present invention in greater detail by way of Examples and Comparative Examples. It is to be noted, however, that the present invention is not limited to the following Examples. The following summarizes details of Examples, including the test methods and materials used in Examples.

Test Methods

Adhesion (Handling Properties) of Dental Composition for Stainless Steel Plate at 25° C.

The dental composition (paste) obtained in the Example or Comparative Example described below was degassed in vacuum, and charged into a syringe. The paste was left to stand at 25° C. for 24 hours to prepare a specimen for adhesion testing. The paste in the syringe was then extruded into a cup having a volumetric dimensions measuring 11 mm in bottom face diameter, 13 mm in top face diameter, and 8 mm in height. Separately, a jig having an end with a stainless-steel cylinder (10 mm in diameter x 5 mm; a stainless steel plate) was attached to a compact table-top tester (EZ Test, manufactured by Shimadzu Corporation). The bottom surface of the stainless-steel cylinder on the jig was then gently brought into contact with the paste surface, and the maximum stress of when the jig was lifted at a crosshead speed of 50 mm/min was measured at 25° C. The test was repeated twice, and the mean value was calculated to find the adhesion. The measured adhesion was used as an index of handling properties. Smaller adhesion values indicate more desirable handling properties. The adhesion is preferably 4.0 N or less, more preferably 3.0 N or less, even more preferably 2.0 N or less, particularly preferably 1.5 N or less, most preferably 1.0 N or less.

Polymerization Shrinkage Stress of Dental Composition

The dental composition (paste) obtained in the Examples or Comparative Example described below was charged into a ring-shaped mold (stainless steel; 5.5 mm in inner diameter×0.8 mm in thickness) placed on a 4.0 mm-thick glass plate. The glass plate was used after being sandblasted with an alumina powder having an particle diameter of 50 μm. A stainless-steel jig (Ø=5 mm), coupled to a universal testing machine (Autograph AG-I, 100 kN, manufactured by Shimadzu Corporation), was then placed on the paste filling the mold. The paste was then cured by applying light for 20 seconds through the glass plate, using a dental LED photoirradiator for polymerization (PenCure 2000 manufactured by J. Morita Corp.). The polymerization shrinkage stress due to curing by the polymerization reaction of dental composition initiated by photoirradiation was measured with the universal testing machine (n=3). Table 1 shows the polymerization shrinkage stress as a mean value of measured values. The polymerization shrinkage stress is preferably 12.0 MPa or less, more preferably 11.0 MPa or less, even more preferably 10.0 MPa or less, particularly preferably 9.8 MPa or less.

Flexural Strength of Cured Product

The dental composition obtained in the Example or Comparative Example described below was degassed in vacuum, and charged into a stainless-steel mold (dimensions: 2 mm×2 mm×25 mm). With the dental composition being pressed between glass slides from top and bottom, light was applied through the glass slides from both sides to cure the dental composition and obtain a cured product specimen. Here, light was applied at 5 points each side, 10 seconds at each point, using a dental LED photoirradiator for polymerization (PenCure 2000 manufactured by J. Morita Corp.). A total of 5 specimens were prepared for each Example and Comparative Example. The specimen was stored in 37° C. distilled water for 24 hours after being taken out of the mold. The specimens were tested in a three-point flexural test conducted in compliance with JIS T 6514:2015 and ISO 4049:2009 at a span length of 20 mm and a crosshead speed of 1 mm/min, using a precision universal testing machine (Autograph AG-I, 100 kN, manufactured by Shimadzu Corporation). From the measured values, a mean value was calculated for each specimen to find the flexural strength. The flexural strength is preferably 100 MPa or more, more preferably 120 MPa or more, even more preferably 140 MPa or more, particularly preferably 150 MPa or more.

Transparency of Cured Product

A cover glass was placed on a glass slide, and, with a stainless-steel mold (Ø=20 mm, thickness=1 mm) set on the cover glass, the dental composition obtained in the Example or Comparative Example described below was filled into the mold until there was a slight overflow. With another cover glass and an overlying glass slide placed on the dental composition, a downward force was applied to push out the excess dental composition from the mold. The dental composition was then cured by applying light from both sides, 2 minutes each side, using an LED polymerizer (Light V, manufactured by J. Morita Corp.). After curing, the cover glasses, glass slides, and mold were removed to obtain a cured product specimen.

The transparency of the cured product was evaluated in compliance with JIS Z 8722:2009, Condition c, using a spectrophotometer (CM-3610d manufactured by Konica Minolta Japan, Inc.) (n=1). Specifically, the cured product was measured for lightness (L1) and lightness (L2), and the difference between these values (ΔL=L1−L2) was calculated as an index of transparency. Here, L1 represents a lightness index L* in the L*a*b* color system of JIS Z 8781-4:2013 in a measurement of chromaticity against a standard white plate placed behind the specimen, and L2 represents a lightness index L* in the L*a*b* color system in a measurement of chromaticity against a standard black plate placed behind the same specimen. Larger values of ΔL mean higher transparency. For a closer appearance to natural teeth, ΔL is preferably 20.0 or more, more preferably 25.0 or more, even more preferably 30.0 or more.

Materials

Polyfunctional (meth)acrylic monomer (a-1) having an aromatic ring but no hydroxyl group D2.6E: 2,2-Bis(4-methacryloyloxypolyethoxyphenyl)propane (average addition number of ethyleneoxy groups: 2.6)

D4E: 2,2-Bis(4-methacryloyloxypolyethoxyphenyl)propane (average addition number of ethyleneoxy groups: 4)

D10E: 2,2-Bis(4-methacryloyloxypolyethoxyphenyl)propane (average addition number of ethyleneoxy groups: 10)

Polyfunctional (meth)acrylic monomer having an aromatic ring and a hydroxyl group Bis-GMA: 2,2-Bis[4-(3-methacryloyloxy-2-hydroxypropoxy)phenyl]propane Polyfunctional (meth)acrylic monomer (a-2) having an alicyclic skeleton TCDDM: Tricyclo[5.2.1.0$^{2,6}$]decanedimethanol dimethacrylate HBPEM-10: Ethylene oxide-modified hydrogenated bisphenol A dimethacrylate (average number of ethyleneoxy groups added: 10)

Polyfunctional (meth)acrylic monomer having no alicyclic skeleton

TEGDMA: Triethylene glycol dimethacrylate

Polymerization initiator

CQ: Camphorquinone

TPO: 2,4,6-Trimethylbenzoyldiphenylphosphine oxide

Polymerization accelerator

PDE: Ethyl 4-(N,N-dimethylamino)benzoate

Polymerization inhibitor

BHT: 3,5-di-t-Butyl-4-hydroxytoluene

Filler

Fillers obtained in the Production Examples below.

Production Example 1

Production of Inorganic Filler (UF2.0)

A three-neck flask was charged with 100 parts by mass of a barium boroaluminosilicate glass GM27884 UltraFine UF2.0 (manufactured by Schott; average particle diameter: 2.0 μm), 1.4 parts by mass of γ-methacryloyloxypropyltrimethoxysilane, and 173 parts by mass of toluene, and the mixture was stirred at room temperature for 2 hours. After removing toluene under reduced pressure, the mixture was vacuum dried at 40° C. for 16 hours, and was heated at 90° C. for 3 hours to obtain an inorganic filler (UF2.0) having a surface-treated layer.

Production Example 2

Production of Inorganic Filler (NF180)

A three-neck flask was charged with 100 parts by mass of a barium boroaluminosilicate glass GM27884 NanoFine180 (manufactured by Schott; average particle diameter: 0.18 μm), 7 parts by mass of γ-methacryloyloxypropyltrimethoxysilane, and 173 parts by mass of toluene, and the mixture was stirred at room temperature for 2 hours. After removing toluene under reduced pressure, the mixture was vacuum dried at 40° C. for 16 hours, and was heated at 90° C. for 3 hours to obtain an inorganic filler (NF180) having a surface-treated layer.

Production Example 3

Production of Inorganic Filler (UF1.0)

A three-neck flask was charged with 100 parts by mass of a barium boroaluminosilicate glass GM27884 UltraFine UF1.0 (manufactured by Schott; average particle diameter: 1.0 μm), 5 parts by mass of γ-methacryloyloxypropyltrimethoxysilane, and 173 parts by mass of toluene, and the mixture was stirred at room temperature for 2 hours. After removing toluene under reduced pressure, the mixture was vacuum dried at 40° C. for 16 hours, and was heated at 90° C. for 3 hours to obtain an inorganic filler (UF1.0) having a surface-treated layer.

Production Example 4

Production of Inorganic Filler (Ar130)

One-hundred parts by mass of a near spherical ultrafine particle Aerosil 130 (a ultrafine particle produced by flame hydrolysis, manufactured by Nippon Aerosil Co., Ltd.; average particle diameter: 0.02 μm) was surface treated with forty parts by mass of γ-methacryloyloxypropyltrimethoxysilane to obtain an inorganic filler (Ar130).

Production Example 5

Production of Organic-Inorganic Composite Filler (CF)

A paste was prepared by adding and mixing 100 parts by mass of NF180 (inorganic filler obtained in Production Example 2) with 100 parts by mass of a 1:1 mixture of Bis-GMA and TEGDMA (mass ratio) dissolving 1 mass % of azobisisobutyronitrile (AIBN) as a polymerization initiator. The paste was subjected to thermal polymerization at 100° C. for 5 hours in a reduced pressure atmosphere. The resultant cured product was pulverized with a vibration ball mill until the particles had an average particle diameter of 5 μm. This was followed by a surface treatment, in which 100 g of the pulverized filler was refluxed at 90° C. for 5 hours in a 200 mL ethanol solution of 2 mass % γ-methacryloyloxypropyltrimethoxysilane to obtain an organic-inorganic composite filler (CF).

Examples 1 to 8 and Comparative Examples 1 to 4

The materials shown in Table 1 were mixed in the proportions shown in Table 1 to obtain a dental composition. The dental composition was evaluated for various physical properties using the test methods described above. The results are presented in Table 1.

TABLE 1

| | | | Ex. 1 | Ex. 2 | Ex. 3 | Ex. 4 | Ex. 5 | Ex. 6 | Ex. 7 | Ex. 8 | Com. Ex. 1 | Com. Ex. 2 | Com. Ex. 3 | Com. Ex. 4 |
|---|---|---|---|---|---|---|---|---|---|---|---|---|---|---|
| Polymerizable monomer | | parts by mass | 27 | 27 | 27 | 27 | 27 | 27 | 27 | 25 | 27 | 27 | 27 | 27 |
| | D2.6E | mass %[1)] | 60 | 80 | 90 | 30 | | | 60 | 65 | | | 60 | 20 |
| | D4E | mass %[1)] | | | | 30 | 60 | | | | | | | |
| | D10E | mass %[1)] | | | | | | 60 | | | | | | |
| | Bis-GMA | mass %[1)] | | | | | | | | | 60 | 60 | | |
| | TCDDM | mass %[1)] | 40 | 20 | 10 | 40 | 40 | 40 | | 35 | | 40 | | 80 |
| | HBPEM-10 | mass %[1)] | | | | | | | 40 | | | | | |
| | TEGDMA | mass %[1)] | | | | | | | | | 40 | | 40 | |
| Filler | UF2.0 | parts by mass | 70 | 70 | 70 | 70 | 70 | 70 | 70 | | 70 | 70 | 70 | 70 |
| | NF180 | parts by mass | 3 | 3 | 3 | 3 | 3 | 3 | 3 | | 3 | 3 | 3 | 3 |
| | UF1.0 | parts by mass | | | | | | | | 23 | | | | |
| | Ar130 | parts by mass | | | | | | | | 3 | | | | |
| | CF | parts by mass | | | | | | | | 49 | | | | |
| Polymerization initiator | CQ | parts by mass | 0.2 | 0.2 | 0.2 | 0.2 | 0.2 | 0.2 | 0.2 | 0.2 | 0.2 | 0.2 | 0.2 | 0.2 |
| | TPO | parts by mass | 0.3 | 0.3 | 0.3 | 0.3 | 0.3 | 0.3 | 0.3 | 0.3 | 0.3 | 0.3 | 0.3 | 0.3 |
| Polymerization accelerator | PDE | parts by mass | 0.2 | 0.2 | 0.2 | 0.2 | 0.2 | 0.2 | 0.2 | 0.2 | 0.2 | 0.2 | 0.2 | 0.2 |
| Polymerization inhibitor | BHT | parts by mass | 0.1 | 0.1 | 0.1 | 0.1 | 0.1 | 0.1 | 0.1 | 0.1 | 0.1 | 0.1 | 0.1 | 0.1 |
| Results of evaluation for dental composition | Adhesion | N | 0.9 | 1.7 | 2.0 | 0.9 | 1.0 | 1.2 | 2.2 | 0.8 | 4.1 | 4.7 | 1.1 | 0.9 |
| | Polymerization shrinkage stress | MPa | 9.5 | 10.1 | 10.9 | 9.8 | 9.6 | 10.0 | 11.0 | 9.6 | 13.6 | 9.3 | 12.3 | 9.5 |
| | Flexural strength of cured Product | MPa | 144 | 151 | 150 | 145 | 138 | 148 | 123 | 103 | 153 | 97 | 148 | 113 |
| | Transparency of cured product | | 32 | 30 | 27 | 31 | 31 | 32 | 34 | 28 | 33 | 33 | 32 | 18 |

[*1)]Mass fraction in polymerizable monomer

As shown in Table 1, it was confirmed that the dental compositions of the present invention were capable of producing cured products having desirable mechanical strength and excellent transparency. The dental compositions of the present invention were also shown to have low polymerization shrinkage stress with good handling properties as demonstrated by the weak adhesion to the stainless steel plate used to simulate a filling instrument.

The invention claimed is:

1. A dental composition, comprising:
   (A) a polymerizable monomer;
   (B) a filler; and
   (C) a polymerization initiator,
   wherein the polymerizable monomer (A) comprises (a-1) a polyfunctional (meth)acrylic monomer comprising an aromatic ring, but no hydroxyl group, and (a-2) a polyfunctional (meth)acrylic monomer comprising an alicyclic skeleton,
   wherein the polyfunctional (meth)acrylic monomer (a-1) and the polyfunctional (meth)acrylic monomer (a-2) are comprised in the polymerizable monomer (A) in 90 mass % or more, and
   wherein the polyfunctional (meth)acrylic monomer (a-1) and the polyfunctional (meth)acrylic monomer (a-2) have an (a-1)/(a-2) mass ratio in a range of from 30/70 to 95/5.

2. The dental composition of claim 1, wherein the polyfunctional (meth)acrylic monomer (a-1) is an aromatic di(meth)acrylic acid ester of formula (1),

[Chem. 1]

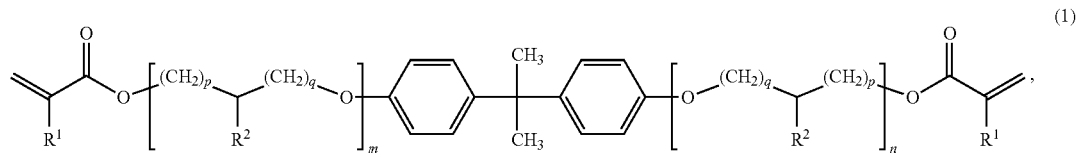

(1)

wherein
$R^1$ is H or a methyl group,
$R^2$ is H or an alkyl group having 1 to 3 carbon atoms,
p and q are independently an integer in a range of from 0 to 6,
m and n are independently an integer of 0 or more,
wherein an average addition number of alkyleneoxy groups as represented by an average of the sum of m and n per molecule, is in a range of from 2 to 30.

3. The dental composition of claim 1, wherein the polyfunctional (meth)acrylic monomer (a-1) is 2,2-bis(4-methacryloyloxy (poly) ethoxyphenyl) propane, with an average addition number of ethyleneoxy groups in a range of from 2 to 30.

4. The dental composition of claim 1, wherein the total number of carbon atoms constituting the alicyclic skeleton of the polyfunctional (meth)acrylic monomer (a-2) is in a range of from 5 to 20.

5. The dental composition of claim 1, wherein the polyfunctional (meth)acrylic monomer (a-2) is at least one selected from the group consisting of tricyclo[5.2.1.0$^{2,6}$]decanedimethanol di(meth)acrylate and ethylene oxide-modified hydrogenated bisphenol A di(meth)acrylate.

6. The dental composition of claim 1, having an adhesion of 4.0 N or less for a stainless steel plate at 25° C.

7. The dental composition of claim 1, having a polymerization shrinkage stress of 12.0 MPa or less.

8. The dental composition of claim 1, wherein the polyfunctional (meth)acrylic monomer (a-2) comprises tricyclo[5.2.1.0$^{2,6}$]decanedimethanol di(meth)acrylate.

9. The dental composition of claim 1, wherein the polyfunctional (meth)acrylic monomer (a-2) comprises ethylene oxide-modified hydrogenated bisphenol A di(meth)acrylate.

10. The dental composition of claim 8, wherein the polyfunctional (meth)acrylic monomer (a-2) comprises ethylene oxide-modified hydrogenated bisphenol A di(meth)acrylate.

11. The dental composition of claim 1, wherein the polyfunctional (meth)acrylic monomer (a-1) and the polyfunctional (meth)acrylic monomer (a-2) are comprised in the polymerizable monomer (A) in 100 mass %.

12. The dental composition of claim 2, wherein the average addition number of ethyleneoxy groups in a range of from 2 to 20.

13. The dental composition of claim 2, wherein the average addition number of ethyleneoxy groups in a range of from 2 to 12.

14. The dental composition of claim 2, wherein the average addition number of ethyleneoxy groups in a range of from 2 to 7.

15. The dental composition of claim 2, wherein the average addition number of ethyleneoxy groups in a range of from 2 to 3.

16. The dental composition of claim 2, wherein the average addition number of ethyleneoxy groups in a range of from 2.1 to 7.

17. The dental composition of claim 2, wherein the average addition number of ethyleneoxy groups in a range of from 2.1 to 2.9.

18. The dental composition of claim 1, wherein the total number of carbon atoms constituting the alicyclic skeleton of the polyfunctional (meth)acrylic monomer (a-2) is in a range of from 6 to 18.

19. The dental composition of claim 1, wherein the total number of carbon atoms constituting the alicyclic skeleton of the polyfunctional (meth)acrylic monomer (a-2) is in a range of from 8 to 12.

20. The dental composition of claim 1, wherein the total number of carbon atoms constituting the alicyclic skeleton of the polyfunctional (meth)acrylic monomer (a-2) is in a range of from 9 to 11.

* * * * *